(12) United States Patent
Berlowitz et al.

(10) Patent No.: US 8,809,029 B2
(45) Date of Patent: Aug. 19, 2014

(54) POND SYSTEM FOR ALGAE GROWTH AND HARVESTING

(75) Inventors: Paul J. Berlowitz, Glen Gardner, NJ (US); P. Hugh Helferty, New Hope, PA (US)

(73) Assignee: ExxonMobil Research and Engineering Co., Annandale, NJ (US)

( * ) Notice: Subject to any disclaimer, the term of this patent is extended or adjusted under 35 U.S.C. 154(b) by 166 days.

(21) Appl. No.: 13/272,742

(22) Filed: Oct. 13, 2011

(65) Prior Publication Data

US 2013/0095544 A1 Apr. 18, 2013

(51) Int. Cl.
- *C12P 5/00* (2006.01)
- *C12M 1/00* (2006.01)
- *A01G 33/00* (2006.01)
- *A01G 1/00* (2006.01)
- *C12N 1/12* (2006.01)

(52) U.S. Cl.
CPC ............... *A01G 1/00* (2013.01); *C12M 21/02* (2013.01); *A01G 33/00* (2013.01); *C12M 23/18* (2013.01); *C12P 5/00* (2013.01); *C12M 23/38* (2013.01); *C12M 23/20* (2013.01); *C12N 1/12* (2013.01)
USPC ........................................................ 435/166

(58) Field of Classification Search
CPC ....................................................... C02F 1/006
USPC .......................................................... 435/166
See application file for complete search history.

(56) References Cited

U.S. PATENT DOCUMENTS

| | | |
|---|---|---|
| 5,541,056 A | 7/1996 | Huntley et al. |
| 7,662,616 B2 | 2/2010 | Hazlebeck et al. |
| 7,687,261 B2 | 3/2010 | Hazlebeck et al. |
| 2011/0023360 A1* | 2/2011 | Ryan et al. ............ 47/62 C |
| 2011/0138682 A1* | 6/2011 | Demaris et al. ............ 44/385 |

* cited by examiner

*Primary Examiner* — Ruth Davis
(74) *Attorney, Agent, or Firm* — David M. Weisberg (57) ABSTRACT

Management of a pond for algae growth and harvesting is facilitated by use of a cover system. The cover system can include one or more types of cover portions for management of various interactions between a pond and an ambient environment, such as management of incident light, thermal management, facilitating product recovery, and management of gas diffusion. The cover system can be used in conjunction with both active and passive mixing devices.

6 Claims, 1 Drawing Sheet

POND SYSTEM FOR ALGAE GROWTH AND HARVESTING

FIELD OF THE INVENTION

Systems and methods related to the design and operation of algae growth ponds are provided.

BACKGROUND OF THE INVENTION

One potential source of biofuels is to use algae to generate molecules that are suitable for use as fuels. For example, algae, like plants, can generate lipid molecules. Some lipid molecules have a general structure and molecular weight suitable for making diesel additives or can be converted or used as is in diesel fuel, such as fatty acid methyl esters (FAME). It may also be possible to refine certain algae lipids into conventional fuels or fuel blending stocks including gasoline, diesel, and jet fuel. However, many challenges remain in developing commercial scale production techniques for biofuels based on algae production.

Although hybrid systems exist, photosynthetic algae are typically grown in one of two environments—in an open pond environment, or in a closed system such as a photobiorector. One advantage of an open pond is cost, as an open pond can be constructed easily and is relatively inexpensive to operate. Open ponds typically use gravity and/or a paddle wheel to move and mix algae growing within a circular or raceway pond. Open ponds can be made quite large, with sizes of an acre or even several acres being possible for a single pond. An open pond environment also provides high algae growth rates, as a pond can support growth rates that can allow some types of algae to double in number and/or biomass in less than 24 hours.

Unfortunately, open ponds are typically subject to the ambient weather (e.g., temperature, rainfall) and other conditions of the environment surrounding the pond. For example, an open pond is subject to contamination from outside organisms that may compete with or consume the algae being grown. Gases introduced to enhance growth rates in the pond, such as $CO_2$, can be partially lost through the open surface of the pond if the gases are not captured by the algae with sufficient efficiency. Another potential disadvantage of an open pond is water exchange with the surrounding environment. Many ponds have a large surface area and/or a relatively large ratio of surface area to volume. The large ratio of surface area to volume is typically due to the ponds having a relatively shallow depth, typically about 15 cm to about 75 cm. Because evaporation is proportional to the exposed surface area of a body of water, evaporation of water from the pond can require addition of substantial make-up water in order to maintain a constant concentration. An open pond is also subject to dilution by excessive rain.

Still other potential difficulties with open ponds are related to the harvesting of desired products. Any product secreted by the algae in a pond may evaporate to an extent, or be consumed by bacteria and/or other organisms, resulting in loss of product. For this reason, algae are conventionally first grown and then processed in a series of steps that extract products (e.g. oils, proteins). Concentration and processing of the algae can be complex, as algae typically grow at concentrations in water of less than about 1000 ppm and, more commonly, about 200 ppm to about 400 ppm.

A closed photobioreactor (PBR) system can mitigate several of the problems described above. A PBR system is typically sealed to reduce or prevent contamination from environmental sources. Gasses that evolve from the algae, and gases introduced to grow the algae, can also be managed to a greater extent. Additionally, the algae can be mixed to an extent that optimizes average solar exposure. Water evaporation or dilution can also be controlled or eliminated. Typically, closed photobioreactors enhance the rate of algae growth by 50-100% when compared to open pond systems. However, closed photobioreactor systems are typically much smaller than open ponds, with many photobioreactors (i.e., typically hundreds to thousands) needed per acre of land to achieve the same productivity. Further, relative to a pond, the construction and operation of closed photobioreactor systems is expensive and complicated. Additionally, even during ideal operation, the algae are still not concentrated to greater than a few 1000 s of ppm—although values of up to 1% and above have been reported.

SUMMARY OF THE INVENTION

In the present invention, cover systems and methods employing the same are provided for growing algae and/or managing an algae growth pond to enhance algae growth, lipid production and/or lipid harvesting. The pond can be any convenient type of pond for algae growth or lipid production. Preferably, the pond is a raceway pond.

The cover system can be a single unitary structure. Alternatively, the cover system can be a modular system. Further, different types of covers can be used alone or in combination to perform different functions. The cover system, whether comprising a single structure or multiple modules, can cover the entire surface area of the pond or one or more portions of the pond surface area. Preferably, however, the cover system covers one or more portions, but not the entirety, of the pond surface area.

Accordingly, a system for growing algae is provided. The system includes a pond for growing algae, the pond being in communication with an ambient environment. A cover system is used to cover at least 10% of the surface of the pond. The cover system includes one or more types of cover portions that may be used alone or together in any combination. A first type of cover portion has a thermal management coating that absorbs or reflects at least one of ultraviolet, actinic and/or infrared light. A second type of cover portion increases $CO_2$ utilization in the pond by at least about 5% relative to the pond in an uncovered state. A third type of cover portion reduces at least one of (a) water lost due to evaporation from the pond, or (b) water gained due to absorption of rainwater by the pond, by at least about 5% relative to the pond in an uncovered state. A fourth type of cover portion facilitates capture of hydrocarbons generated by algae in the pond. A fifth type of cover portion selectively allows diffusion of $O_2$ relative to $CO_2$. A sixth type of cover portion allows at least about 50% of incident actinic light intensity to pass through to a pond surface. Several of the above examples may also serve to limit evaporation, contamination and/or provide a mostly impermeable barrier to gas exchange with the environment. As stated, each of these types of cover portions that may be used alone, or together, in any combination.

Similarly, a pond management system for an algae growth pond is provided. Again, the pond management system includes a cover system that corresponds to at least a portion of the surface area of a pond. The cover system includes a first cover portion that allows at least about 50% of incident actinic light intensity to pass through to the surface of the pond. The pond management system further includes a primary mixing device, such as a paddle wheel, configured to generate a flow within the pond. At least one secondary mixing device is also included. The at least one secondary mixing device can be attached to a floor of the pond or a wall of the pond. Optionally, any of the other types of cover portions previously described can be additionally utilized in the pond management system.

Finally, methods for managing a pond that employ one or more of the above identified cover portions are provided. A first method for managing a pond comprises at least two steps. The first step is covering a first portion of a pond with a first cover portion that allows at least 50% of actinic light to pass through the first cover portion. The second step is covering a second portion of the pond with a second cover portion that selectively allows diffusion of $O_2$ relative to $CO_2$. A second method for managing a pond comprises at least five steps. The first step is covering a first portion of a pond with a first cover portion that allows at least 50% of actinic light to pass through the first cover portion. The second step is covering a second portion of the pond with a second cover portion that has a lipophilic surface that facilitates capture of hydrocarbons generated by the algae in the pond. The third step is exposing algae within the pond to conditions effective for accumulation of a product. The fourth step is triggering secretion of the accumulated product. The fifth step is collecting the secreted product using the second cover portion. Ideally, the final algae concentration within the pond after the steps of triggering secretion of the accumulated product and collecting the secreted product is at least about 50% of the first algae concentration. Optionally, any of the other types of cover portions previously described can be additionally utilized in the two methods.

DETAILED DESCRIPTION

Definitions

A "cover system" refers to a contiguous or non-contiguous cover for a pond. Thus, separate structures that are used to cover a pond but that do not otherwise touch are included within the definition of a cover system. One option for building a cover system is to use a unitary construction, where the entire cover is formed as a single cover piece. Alternatively, a cover system may be composed of one or more separate pieces. The one or more separate pieces may be joined together, or the pieces may simply be in contact with each other, or the pieces may not have contact with each other. Separate pieces that are used to form a cover or cover system are referred to here as "cover modules." A "cover portion" refers to any portion of a cover system. Thus, a cover portion can represent a part of a cover having a unitary construction, or one or more modules used to form a modular cover, or a portion of a module.

Algae Growth Pond and General Cover Structure

The inventive structures and methods are designed for use with ponds, and, more particularly, the structures and methods scale well for larger size growth environments. The inventive structures and methods are generally used with ponds having a size of at least about 0.01 acres, especially including ponds of at least about 1 acre, at least about 10 acres and at least about 20 acres. In general, the advantages of the cover systems described herein will increase with increasing pond size.

The size of a cover structure does not need to equal the entire surface area of a pond, but greater protection will be provided for a pond as the surface area of the cover approaches the surface area of the pond. On the other hand, as the pond size increases, the need to cover the entire surface of the pond is reduced. Overall goals for a pond cover, which will dictate the total area of the pond that needs to be covered, may include increasing $CO_2$ utilization by the algae in a pond and decreasing the amount of water loss due to evaporation. For example, it is generally desirable to have a $CO_2$ utilization of at least 90% of $CO_2$ added to a pond. With regard to evaporation, the importance of evaporation reduction increases in hotter and/or drier climates. An evaporation rate reduction of at least about 25% relative to an open pond is beneficial, but in hot and/or dry climates it may be necessary to reduce the evaporation rate by at least 50%, or more preferably at least 75%.

Increasing the area of a pond cover relative to the surface area of a pond will typically improve the $CO_2$ utilization of a pond. Increasing the pond cover area will also typically reduce the amount of water loss due to evaporation. Even a pond cover that covers only 25% of the surface area of a pond will provide some benefit. Increasing benefits will be realized with greater coverage areas, such as a pond cover corresponding to at least about 50% of the surface area of a pond, or alternatively at least about 75% of the surface area, or possibly at least about 90% of the surface area. It is noted that for most ponds, the benefits of a pond cover can typically be realized without needing to cover paddle wheel structures. The portion of the pond surface area corresponding to the paddle wheel is small relative to the total surface area and becomes proportionally smaller as the pond increases in size. As a result, the above benefits can be increasingly realized without covering the paddle wheel itself. Similarly, other structures in a pond that would be awkward to cover and that correspond to a small portion of the surface area can be left uncovered. A cover system that does not result in covering paddle wheels and/or other structures in a pond will correspond to a cover system that covers less than 100% of the surface area of the pond. Depending on the size of the pond, leaving a paddle wheel uncovered may result in a cover system that covers 99% of the pond surface area or less, or 95% of the pond surface area or less. This includes potentially having an area in the vicinity of a paddle wheel that is also left uncovered. If additional structures and/or other additional portions of a pond are left uncovered, the resulting cover system may cover 90% or less of the pond, or 70% or less of the pond, or even 50% or less of the pond.

Any convenient pond structure can be used in various aspects of the invention. One example of a suitable pond is a raceway pond. Raceway ponds are generally preferred due to their relatively uniform fluid dynamics. The intermediate divider for the tracks in a raceway pond also provides a suitable support for a pond cover.

Figure 1:
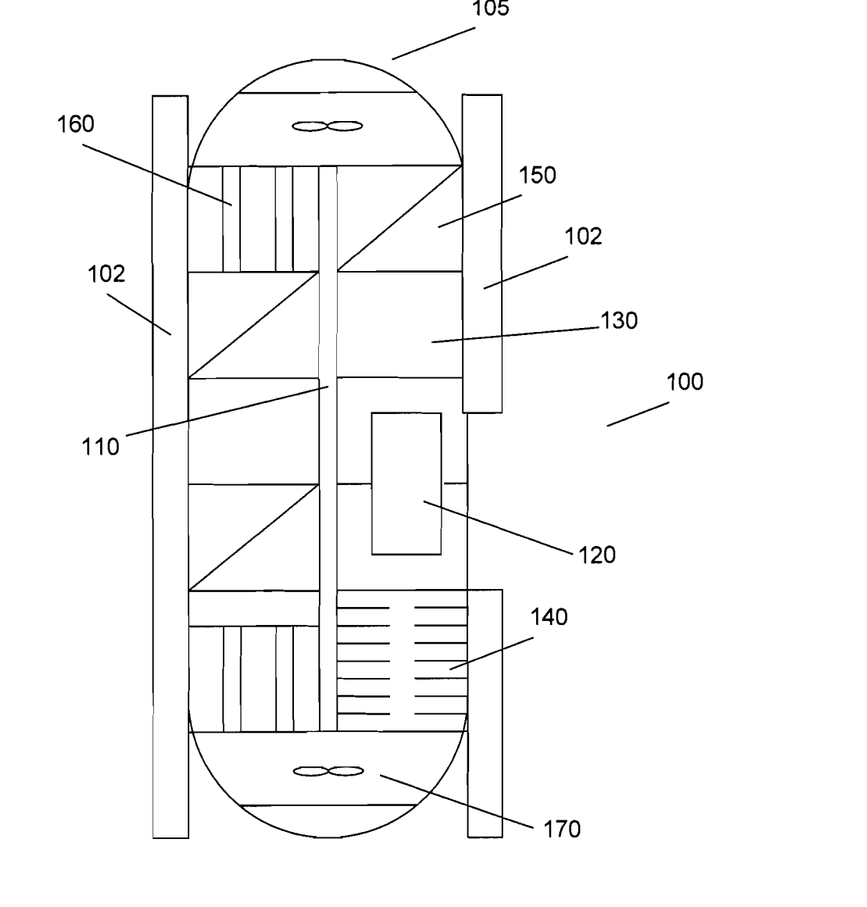
FIG. 1 schematically shows an example of a pond that includes a pond cover system according to one aspect of the invention.

FIG. 1 schematically shows an example of a top down view of a raceway pond 100 with a partial cover. In the example shown in FIG. 1, the partial cover is composed of cover modules 130, 140 and 150 of different types having different functionality. Alternatively, a pond cover having a single unified structure can be used.

A algae pond generally includes a mechanism for inducing a flow into the pond, such as a paddlewheel 120 shown in FIG. 1. The paddlewheel 120 provides a defined current within the pond, allowing for control of a bulk flow rate of the water in the pond 100. Additional modifications to the flow pattern within a pond can be made by allowing the cover to come into contact with the water surface at various locations, by including active and/or passive flow modification structures within the pond, or by other convenient methods. Alternative methods for introducing flow into the pond include simple gravity flow or pumping of water by conventional methods.

The pond can have any convenient width. In some aspects, the width of the pond is selected to facilitate bridging the width of the pond with a cover. In this discussion, the width of a pond is defined as a distance between two structures that can serve as bridging or resting surfaces for a cover. In general, the cover is supported by, and preferably attached to, the bridging or resting surfaces. For example, in FIG. 1, raceway pond 100 includes an external perimeter 105 and an internal divider 110. A divider can be any convenient structure that maintains separation between the two flow paths of the raceway 100. For the pond in FIG. 1, the width of the pond corresponds to the distance from the external perimeter 105 to internal divider 110. Note that the width of a pond structure can, but preferably does not, vary along the length of a pond. Typically the length to width ratio of a pond is between 2 and 50, more commonly between 5 and 15. For ponds having a surface area greater than 1 acre (approximately 0.4 hectar), a length to width ratio of 10 to 15 is preferred. Longer length to width ratios require more pumping force, such as larger paddlewheels or multiple paddlewheels, while wider ponds are more difficult to mix.

Any length to width ratio in the typical range is acceptable. Preferably, however, the length width ratio is at least 5 and preferably at least 10 for ponds of 1 acre or more in size. Values larger than 10 are preferred for the reasons already stated and, also, to provide widths more easily bridged by cover structures. For example, a 1 acre pond with a length to width ratio of 15 corresponds to a pond with a width of about 54 feet (approximately 16.5 meters). If the divider in the center of the raceway is used as one support location, a cover structure with a width of about 27 feet (approximately 8.2 meters) can be used.

The pond can have any convenient depth. Although not preferred, the depth can also vary along the length and/or width of the pond. Due to absorption of light by algae, in a typical pond only the first few centimeters of the pond will experience a light intensity that is at least 10% of the light intensity incident on the pond surface. Depending on the density of the algae and the concentration of chlorophyll in the cells, the depth of water in the pond experiencing more than 10% of the incident light intensity can be 20 cm or less, 10 cm or less, 5 cm or less, 2 cm or less, or even 1 cm or less. As a result, algae below a given depth in a pond will experience little or no light intensity. Having algae experience time periods of little or no light intensity is a condition that occurs naturally in ponds, and the presence or absence and duration of such time periods impacts the photosynthetic efficiency of algae. In general, algae grow faster when the algae are exposed to intermittent light as opposed to continuous light. The optimum depth and mixing requirements of the pond are dependent on the algae species and the corresponding efficiency of the algae for capturing light intensity. For most species, continuous direct sunlight result in a solar radiation level greater than the maximum level that can be used by the algae. This leads to excess light intensity that is wasted primarily as absorbed heat.

In order to provide improved control over the growth and/or lipid production of algae in a pond, it can be beneficial to limit the depth of the pond so that algae in a lower depth (darker) portion of a pond can be returned to the portions of the pond closer to the surface on a desired time scale. In addition, it is easier to maintain a desired amount of mixing or turbulence in a shallow pond, allowing for rapid exchange of algae from darker to lighter regions. As noted above, exposing algae to intermittent light intensity rather than continuous light intensity will typically enhance the growth rate of the algae. For example, based on the operation of the paddlewheel or other device for inducing a flow, water in the pond can have an average circuit time around the pond on the order of hours. In order to achieve intermittent exposure of algae to light intensity, during a full circuit of the pond, it is generally desirable for algae to spend an average of about 10% to about 50% of the pond circuit time in a region having greater than about 10% of the incident light intensity. Alternatively, the average amount of time algae experience at least 10% of the incident light intensity can be at least about 15% of the circuit time, or at least about 20%, or at least about 25%, or about 50% or less, or about 40% or less, or about 30% or less. The preferred amount of time for algae to be exposed to greater than about 10% of the incident light intensity is dependent on a variety of factors, such as the type of algae and the desired balance between algae growth and algae oil production. For example, some algae may have a high rate of photon absorption when exposed to light, but may also need longer periods away from sunlight to achieve efficient growth and/or oil production. Such algae may prefer decreasing amounts of time with exposure to greater than 10% of incident light intensity. For algae that have little or no drop in efficiency when exposed to additional light, the higher amounts of time with exposure to greater than 10% of incident light intensity may be preferred.

For a well-mixed pond, one way of controlling the amount of incident light the algae is exposed to is based on a combination of the algae density in the pond and the depth of the pond. At a given algae density, increasing the depth of the pond will decrease the amount of time algae is exposed to at least 10% of the incident light. This is due to a greater percentage of the pond being far from the surface, and therefore a greater percentage of the pond volume will be below the depth where light is attenuated to less than 10%. The amount of light attenuation is also dependent on the type of algae and the algae concentration. Different algae have different concentrations of chlorophyll, and thus different efficiencies at capturing versus transmitting light. To achieve a desired amount of light attenuation, the depth of the pond is generally selected to be about 100 cm or less and, more typically, about 75 cm or less. Even more typical pond depths will be about 50 cm or less, or about 35 cm or less, or about 30 cm or less. Additionally or alternately, the depth of the pond can be at least about 5 cm, or at least about 10 cm, or at least about 20 cm.

The cover structure can be located at various distances above the surface of a pond. The distance between the cover and the pond will dictate the volume of gas that resides between the surface of the pond and the cover. Preferably, the amount of gas phase volume under the cover is small relative to the liquid volume. A smaller gas volume between the pond surface and the cover potentially provides several benefits. For example, $CO_2$ is a beneficial gas for algae growth that is typically added to an algae growth environment. A given concentration of $CO_2$ within the pond will have a corresponding gas phase partial pressure of $CO_2$ above the pond at equilibrium. A larger gas volume above the pond means that a larger amount of gas phase $CO_2$ will be needed to meet this partial pressure requirement. Any $CO_2$ in this gas phase above the pond corresponds to $CO_2$ that is not directly available for absorption by algae. Additionally, this gas phase $CO_2$ may be lost to the outside environment through any openings in the cover.

Although a lower volume of gas between the pond surface and the cover is desirable, it can also be beneficial to maintain at least some distance between the pond surface and at least a portion of the cover. As noted above, a raceway pond typically includes a paddle wheel or other mechanism for introducing a flow into the pond. Preferably, the flow will cause the algae in the pond to travel around the pond, rather than stagnating in a location and potentially depleting the nutrients in the local environment. Having a cover in contact with the surface of the pond may change the flow characteristics of the water in the vicinity of the contact with the cover. Additionally, some cover portions or modules may have a functional reason for avoiding contact with the pond surface. For example, a cover portion or module that includes a coating to provide a desired type of light transmission or reflection may need an air gap between the coating and the surface of the pond to provide the desired light transmission characteristics. As another example, a cover portion that incorporates photovoltaic cells may not work as intended if the cover portion is in contact with the surface of the pond. In this case, the gap between the pond surface and the cover can be selected to avoid contact between the pond and the cover based on typical water level fluctuations while still minimizing the gap.

The amount of volume between the surface of the pond and the cover should be chosen to provide a desired total volume underneath the cover. Preferably, relative to the total volume underneath the cover, the liquid volume (corresponding to the pond) occupies at least about 90% of the volume, and more preferably at least about 95% of the volume. However, the pond cover should still be effective at lower relative volumes of liquid to gas, such as having liquid correspond to at least 50% of the volume, or at least 75% of the volume.

At the edges of the pond 100, a cover support structure 102 can be included to facilitate placement of the cover. The divider 110 can also optionally include a cover support structure 102. The cover support structure 102 can be as simple as a lip structure. An edge of the cover can be seated on a lip structure to allow the cover to rest at or above the surface of the pond. Alternatively, cover support structure 102 can correspond to a platform that the cover can be attached to. A cover support structure 102 in the form of a platform can be attached to a cover by using clips, bolts, or straps, or the cover can be secured by a type of friction fit with a protruding lip, or the cover can simply rest on the cover support structure.

Optionally, the cover support structure 102, or portions thereof, can be raised or lowered. This causes a corresponding height change in the cover relative to the surface of the pond, and can therefore change the volume of gas supported above the surface of the pond and below the cover. For example, one portion of a cover system can be a cover module suitable for harvesting lipid products from the pond. Depending on the nature of the algae and the rate of lipid production, it could be desirable to have two operating positions for the cover module for harvesting lipid products. In a first position, the cover module is above the surface of the pond, to provide the best flow and mixing characteristics for the pond. In a second position, the cover module is in contact with the surface of the pond to allow for retrieval of lipid products from the surface of the pond. Alternatively, changes in the relative position of the pond surface versus the cover can be made by changing a water level in the pond.

With regard to the cover, in FIG. 1 a variety of cover module types are schematically shown. Several cover modules in FIG. 1 correspond to environmental cover modules 130. Other cover modules include product recovery modules 140 and diffusion modules 150. It is noted that FIG. 1 is a schematic drawing only, and therefore the markings used to distinguish the various cover module types do not imply or require a particular structure for the module. FIG. 1 further indicates environmental modules that include solar collectors 160. Additionally, FIG. 1 shows examples of secondary mixing devices 170.

Environmental Cover Portion or Module

One source of variability for managing a pond exposed to the external environment is water loss to the environment and/or water gain from the environment. When the pond is exposed to direct sunlight during daylight hours, a substantial amount of water can evaporate from the pond. Alternatively, during a rainstorm, a large amount of fresh water of uncontrolled temperature will enter the pond, potentially reducing productivity of algae in the pond due to changes in pH, salinity, temperature, and/or dissolved nutrients and mineral concentrations.

These effects can be mitigated by covering a portion of the pond with an environmental cover. Environmental cover modules are composed of a material suitable for protecting the pond from interaction with the environment while still allowing sunlight to enter the pond. The goal of the environmental cover portions is to reduce or minimize interaction between the pond and the environment and, thereby, reduce interference from the environment. The environmental cover portions reduce or preferably prevent diffusion of gasses across the cover, limit evaporation, and prevent rainwater from directly entering the pond. However, the environmental cover portions do not need to provide a complete or air-tight seal. Instead, the environmental cover portions can just reduce the rate of interaction between the pond and the environment. Preferably, a large pond of 1 acre or greater is predominantly protected by environmental covers which will be sufficient to maintain control over key pond physical and chemical process variables.

As an additional benefit, an environmental cover portion (or optionally other cover portions) can also be configured to collect or capture rainwater that is incident on the cover. Rainwater collected by a cover system would provide a source of water for addition to the pond in a controlled manner. Alternatively, captured rainwater could be used for any other convenient purpose. Capturing rainwater incident on the cover would also prevent damage to the area surrounding the pond due to runoff. Relative to a pond without a cover, an environmental cover typically enables a reduction of the amount of rainwater absorbed by a pond of at least about a 5%, preferably at least about a 10%, more preferably at least about a 20%, and still more preferably at least about a 50%. Additionally or alternately, relative to a pond without a cover, an environmental cover typically enables a reduction of the amount of water lost from a pond due to evaporation of at least about a 5%, preferably at least about a 10%, more preferably at least about a 20%, and still more preferably at least about a 50%. It is noted that a cover system corresponding to 100% of the surface area of a pond could potentially reduce evaporation and/or rainwater absorption by 100%. However, often, the cover system will correspond to less than 100% of the pond surface area, resulting in a reduction of evaporation and/or rainwater absorption of less than 100%, such as less than 99% or less than 95%.

An environmental cover or cover module is defined based on the properties of the cover increasing the partial pressure of $CO_2$ in the volume between the pond surface and the cover and permitting transmission of light intensity. Alternatively, the ability of the pond cover to modify the $CO_2$ gas exchange rate between the pond and the environment can be used in place of increasing the partial pressure of $CO_2$.

With respect to increasing the partial pressure of $CO_2$, a typical value for the atmospheric concentration of $CO_2$ is about 390 ppm. This value is slowly increasing over time and has some variation with position around the earth. In an open pond, the first few centimeters of water near the pond surface will rapidly equilibrate with the atmosphere. If the pond is being injected with $CO_2$ in order to facilitate algae growth, as is typically practiced, the rapid equilibration of the surface of the pond will result in a gradient of $CO_2$ concentration in the pond, with lower concentrations of $CO_2$ near the pond surface due to loss of $CO_2$ to the atmosphere.

An environmental cover module can mitigate this loss of $CO_2$ to the atmosphere by maintaining a higher concentration of $CO_2$ in the gas phase above the pond. This leads to a corresponding higher liquid-phase $CO_2$ concentration by equilibration. The rate of loss of $CO_2$ from the pond to the atmosphere will typically be proportional to the difference in concentration between actual concentration of $CO_2$ in the pond and the equilibrium value. Increasing the concentration (or equivalently the partial pressure) of $CO_2$ in the atmosphere above the pond will therefore reduce the rate of loss of $CO_2$ from the pond. An environmental cover facilitates a build-up of $CO_2$ concentration above the pond by reducing the volume of atmosphere above the pond. For an open pond, the volume of the atmosphere is large enough that emission of $CO_2$ from the pond result in effectively no change in the $CO_2$ content of the surrounding atmosphere. By contrast, an environmental cover over a pond defines a much smaller volume of gas that interacts with the pond. Even if the volume of gas above the pond has some exchange with the atmosphere outside of the pond cover, an environmental cover module can allow the $CO_2$ concentration underneath the cover to increase. It is typical for $CO_2$ to be introduced into ponds in a limited area via one or more sumps that are deeper than the normal pond depth. As the flow moves away from the sump, $CO_2$ is consumed by the algae while oxygen is generated. $CO_2$ loss can be reduced or minimized by locating the pond cover over and/or directly downstream from the $CO_2$ sump(s). When the $CO_2$ is mostly consumed by the algae, a non-covered section can then be used to allow oxygen to rapidly equilibrate to atmospheric levels with minimal loss of $CO_2$.

Relative to the atmospheric concentration, an environmental cover typically enables at least about a 5% increase in $CO_2$ concentration in the gas phase between the pond and the pond cover, preferably at least about a 10% increase, more preferably at least about a 20% increase, and still more preferably at least about a 50% increase or at least about a 100% increase. For example, if the atmospheric concentration of $CO_2$ is 390 ppm, using an environmental cover that enables a 10% increase in $CO_2$ concentration in the gas phase between the pond and the pond cover will result in a gas phase that contains 429 ppm of $CO_2$. It is noted that for the cover system as a whole, the amount of pressure differential that can be maintained may be influenced by the properties of other modules or portions of the cover. Additionally, if the cover corresponds to only a portion of the pond surface area, the pressure differential can be influenced by gas exchange with uncovered portions of the pond.

An environmental cover module can be in contact with the surface of a pond. In such case, there is not a gas phase present between the surface of the pond and the pond cover. Instead, the pond cover serves as a diffusion barrier between the pond and the external atmosphere. Because there is not a gas phase present between the pond and the pond cover, it is difficult to characterize an environmental cover module based on the increase in partial pressure of $CO_2$ that is enabled by the module, although it can be characterized in terms of $CO_2$ that ultimately escapes versus the identical pond where no cover is present. Alternatively, in this situation an environmental cover module can instead be characterized based on the $CO_2$ gas exchange rate between the pond and the surrounding atmosphere.

In an algae growth pond, $CO_2$ is typically injected into the pond to provide sufficient $CO_2$ for algae growth. Unfortunately, some of this $CO_2$ will be lost instead of being consumed by algae, due to loss of the $CO_2$ to the atmosphere. The rate of loss of $CO_2$ corresponds to a $CO_2$ gas exchange rate between the pond and the atmosphere. For a given pond surface area, algae concentration, and input rate for $CO_2$, the amount of $CO_2$ lost to the atmosphere (instead of being consumed by algae) can be measured. This defines a baseline amount of $CO_2$ lost to the atmosphere, which should be proportional to the $CO_2$ gas exchange rate. In an open pond, the amount of $CO_2$ loss is dependent on the utilization of $CO_2$ by the algae in the pond. The utilization rate of $CO_2$ by algae in a pond can vary widely, from as little as 10% to greater than 95%. More typical utilization rates are about 60% to about 95%. The $CO_2$ not utilized by the algae corresponds to $CO_2$ that will be lost to the environment. By using an environmental cover the amount of $CO_2$ lost to the environment can be reduced by at least about 10%, preferably at least about 25%, more preferably at least about 50% and ideally at least about 75%. In some cases, the reduction in $CO_2$ loss can be even greater, resulting in reducing the $CO_2$ loss by at least 90% or at least 95% relative to an open pond under the same conditions.

Another way to characterize an environmental cover is based on the amount of light intensity transmitted by the cover. The environmental cover can be constructed from a material that allows light from desired wavelengths for photosynthesis to enter the pond while potentially excluding some light that is not usable. Typically, the material is at least transparent for light in the visible portion of the spectrum. The cover may be designed to be transparent or reflective to other wavelengths depending on the specific application and thermal management needs. The material can be tailored to be only transparent for actinic light as opposed to all visible light, which corresponds to light wavelengths that are valuable for photosynthesis. Here, the transparency of the material for the environmental cover corresponds to the cover allowing at least about 50% of sunlight incident on the environmental cover portion to enter the pond, preferably at least about 75%, more preferably at least about 80%, even more preferably at least about 85% and ideally at least about 90% or more. Alternatively, transparency may be defined relative to visible light or actinic light, so that at least about 50% of actinic light (or alternatively visible light) incident on the environmental cover portion can enter the pond, preferably at least about 75%, more preferably at least about 80%, even more preferably at least about 85% and ideally at least about 90% or more. The amount of incident light on a pond at any given time can vary from little or no light at night to maximum incident sunlight of about 130 $W/m^2$.

The environmental cover portions or cover modules can be made of any convenient material. Suitable choices for allowing light transmission while inhibiting gas diffusion or exchange include polyethylene, polypropylene, polyvinyl chloride, and/or other polymeric materials. Such materials are relatively inexpensive and can be made with high light transmittance and low gas diffusivity. Other polymers that are easily manufactured into thin sheets that are transparent to light are also appropriate, such as polystyrene or PTFE. The thickness of the material can be selected to allow a desired amount of light transmission. In some cases, if the environmental cover material does not provide sufficient structural strength to bridge the width of a pond, a secondary material may be used to add structural stability. For example, the secondary material may correspond to thicker portions of the same material used for the environmental cover. Alternatively, the environmental cover can include reinforcing strips, bars, or other reinforcing material portions attached on the top, bottom, and/or side surfaces of the cover or cover portion to add structural stability.

In one aspect, the environmental cover is based on a lattice of a rigid structural material that provides the structural framework for the cover. A thin layer polymer sheet is then stretched over the lattice. Based on the structural support provided by the rigid lattice, the polymer layer can be as thin as 0.025 cm or less, preferably 0.01 cm or less, and even more preferably 0.0025 cm or less. The thin polymer layers provide good light transmission while still providing a sufficient barrier to reduce or prevent $CO_2$ gas loss to the environment. Other convenient options for providing structural stability while still allowing a desired amount of light intensity to reach the pond surface can also be used.

As noted above, the amount of protection offered by a pond cover is typically proportional to the amount of surface area covered by the pond cover. One option is to have an environmental cover that corresponds to the entire area of the cover. Alternatively, a pond cover may include a variety of types of covers or cover modules. When multiple types of covers are used, the multiple types of structures can be formed together as a single cover structure, or the cover can be built in a modular fashion, such as by using modules with different characteristics that are assembled in a desired manner to form the pond cover. In this situation, the area corresponding to the environmental cover will be less than the total area of the pond cover, as other types of cover portions/cover modules will also be included in the pond cover system. When more than one type of cover is used, an environmental cover more likely to represent the majority of the cover system (e.g., be the most common type of module). As described above, environmental modules are relatively inexpensive, are transparent to light, and assist in retaining $CO_2$ to increase utilization. Thus, environmental cover modules provide an effective basic cover structure for use in composing an overall cover. Relative to the total surface area of the cover system, the percentage of the cover system corresponding to environmental portions or environmental modules is typically at least about 25% of the cover, preferably at least about 40% of the cover, more preferably at least about 50% of the cover, even more preferably at least about 70% of the cover and ideally at least about 90% of the cover or more.

Diffusion Cover Portions or Modules

During growth of algae, the algae consume carbon dioxide as part of the photosynthesis process. The algae also generate oxygen as a product of the photosynthesis reaction. In a conventional open pond, excess oxygen generated by the algae exits the pond into the outside environment. This oxygen loss is beneficial, as increasing oxygen concentration leads to increasing inhibition of algae growth. Unfortunately, $CO_2$ injected into the pond to facilitate algae growth is also lost to the outside environment. This is especially true for shallow ponds, as $CO_2$ injected into the pond may permeate to the surface of the pond faster than the $CO_2$ can be consumed by algae. Thus, it is beneficial to allow for oxygen loss from a pond while preventing similar loss of $CO_2$.

A diffusion cover or cover module can be used to allow release of oxygen from the pond while still increasing $CO_2$ utilization. The goal of a diffusion cover is to allow selective diffusion of $O_2$ relative to $CO_2$. It is not necessary for the selectivity for $O_2$ to be 100%. Instead, it is sufficient that $O_2$ levels under a pond cover are reduced to a point where inhibition of algae growth is reduced or minimized while still providing an increased concentration of $CO_2$. Because $O_2$ is generated by photosynthesis, without a mechanism for releasing the $O_2$, the amount of $O_2$ generated by an algae growth will quickly lead to a concentration of $O_2$ in a gas phase below the pond cover that is greater than the atmospheric $O_2$ concentration. A diffusion cover provides such a release mechanism. The release of oxygen can also be mediated by limited areas of free gas exchange. While this will also allow $CO_2$ to escape at a more rapid rate, the negative effect of increased oxygen is not necessarily directly correlated and equal to the positive effect of increased $CO_2$ concentration and may depend on environmental conditions and algae species and strain. Given knowledge of these parameters, a choice between competitive diffusion and simple, periodic gas purging (as is often done in photobioreactors) can be made judiciously.

A variety of polymeric materials and composite materials are known that are suitable for forming a diffusion cover. Suitable materials include oxygen ion transport membranes, such as those composed of perovskites or some types of fluorocarbon membranes. Such materials can be supported or bound to a porous polymer film (such as a perforated sheet), or if structurally stable, can be used alone as a diffusion cover material. When bound to a support, the materials can be sprayed on and/or bound with various porous polymers or resins to create a membrane that provides selective $O_2$ gas diffusion enhancement. The spraying or binding of the materials to the porous polymers or resins can be performed using any suitable conventional technique.

Some choices of material for a diffusion cover will result in a cover or cover module that is not transparent to light. While small areas of a pond could be covered with a material that is not transparent, preferably a pond cover is at least partially transparent over the full surface of the cover. To allow this, a selective $O_2$ transport material that is not transparent can be used in combination with a transparent material to form the diffusion cover. One example is a diffusion cover with alternating strips of selective $O_2$ transport material and a transparent material, such as a material described above for use in an environmental cover module. By using alternating strips, the transparent portions of the cover will allow light to reach most or substantially all portions of the pond surface while still providing a reasonable amount of diffusion cover area for permitting diffusion of $O_2$ through the cover. Alternative patterns of alternating transparent and nontransparent materials can also be used including, but not limited to, a checkerboard pattern.

Depending on the material, the thickness of a diffusion membrane may be thin relative to the thickness needed for suitable structural stability. This is due in part to the relationship between the thickness of the diffusion material and the diffusion rate through the diffusion material. In order to allow a desired diffusion rate for oxygen, a diffusion cover can include other materials to provide structural stability. One option is to support the membrane material for allowing diffusion using a framing material that provides structural support, such as polypropylene or polyethylene. Alternatively, framing materials include other polymers, plastics or metals such as stainless steel.

The diffusion cover enables certain relative concentrations (or equivalently partial pressures) of $O_2$ and $CO_2$ that are achieved in the gas phase between a pond cover and the pond surface. As noted above, due to the oxygen generated by algae during photosynthesis, a concentration of oxygen greater than atmospheric will quickly build up between a cover and the pond surface. Typically, the $O_2$ concentration in the gas phase below the pond cover will be greater than the atmospheric $O_2$ concentration by about 20% or less, preferably by about 10% or less, and more preferably by about 5% or less. Still more preferably, some diffusion covers will allow sufficient $O_2$ diffusion so that the $O_2$ concentration below the cover is less than 1% greater than the atmospheric concentration of $O_2$. With regard to $CO_2$, the diffusion can facilitate an increased $CO_2$ concentration below the cover as compared to the atmosphere. Typically, the diffusion cover can enable at least about a 5% increase in $CO_2$ concentration in the gas phase between the pond and the pond cover, preferably at least about a 10% increase, more preferably at least about a 20% increase, still more preferably at least about a 50% increase and ideally at least about a 100% increase.

The portion of the pond covered by the diffusion cover can be selected to allow for release of oxygen so that the average oxygen content in the pond is maintained at a desired level. Diffusion cover modules could be used to cover the full surface of a pond. More typically, a diffusion cover or diffusion cover modules will represent a relatively small portion of the pond surface area or the total cover area. For a pond cover system that corresponds to at least about 90% of the surface area of a pond, the portion of the pond cover system that facilitates oxygen diffusion can be selected based on a mass balance between the expected amount of $O_2$ generation and the desired oxygen concentration below the cover. For example, for a given type of algae, a maximum growth rate (or a maximum desired growth rate) for the algae can be determined. This maximum growth rate will have a corresponding rate of oxygen generation per gram (or other unit of mass) of algae. Multiplying a desired concentration of algae by the pond volume will yield the algae mass. The algae mass can be multiplied the rate of oxygen generation per gram of algae at the maximum growth rate to produce a potential rate of oxygen generation for the pond. For oxygen leaving the volume below the cover, the amount of $O_2$ transported through the diffusion cover sections will correspond to the difference between the $O_2$ concentration on either side of the cover multiplied by the diffusion rate per unit area for the diffusion cover and the diffusion cover area. This yields a mass balance equation, which can be rearranged to solve for the diffusion cover area:

$$\text{Diffusion Cover Area} = (\text{Pond Volume}) \times (\text{Algae Conc.}) \times (O_2 \text{ Generation Rate Per gram of Algae}) / (\Delta O_2 \text{ Concentration}) \times (O_2 \text{ Diffusion Rate})$$

After determining the diffusion cover area, the percentage of the pond surface area and/or the cover area corresponding to the diffusion cover can be readily determined. For example, consider a hypothetical pond with a depth of 10 cm and a total volume of 100 $m^3$. This corresponds to a pond with a surface area of 1000 $m^2$. In this calculation, an algae concentration of 0.1 grams per liter will be used, or 100 grams per $m^3$. At this concentration, at maximum growth the $O_2$ generation rate per gram of algae is 0.01 gram of $O_2$ per hour. Thus, at maximum growth, the pond will generate 100 grams of $O_2$ per hour (corresponding to 100 $m^3 \times 100$ grams algae per $m^3 \times 0.01$ gram $O_2$ per hour).

In this hypothetical example, nearly all of the pond area will be covered, so this example will illustrate a conservative calculation where it is assumed that no $O_2$ will escape through an open portion of the cover. For the cover portions that correspond to a diffusion cover, the rate of diffusion of $O_2$ is 0.4 grams of $O_2$ per hour per $m^2$ of diffusion cover area for each 1 kPa of pressure differential across the diffusion cover. The rate of $O_2$ diffusion through other cover portions is assumed to be zero for this conservative calculation. In this example, it is desired to have an increase in $O_2$ partial pressure below the cover relative to the environment of 1 kPa or less. Based on these values, 250 $m^2$ of diffusion cover surface area is needed to allow for diffusion of 10,000 g of $O_2$ per hour across the diffusion cover portions. Thus, this hypothetical conservative calculation would result in selecting a pond cover system where 25% of the pond surface area corresponds to diffusion cover modules.

The portion of a pond surface that is covered by a diffusion cover can be about 25% of the pond surface area or less, or about 20% or less, or about 15% or less, or about 10% or less, or about 5% or less. The portion of the pond cover that corresponds to a diffusion cover or diffusion cover module is dependent on the permeability of the diffusion cover. A diffusion cover with a membrane that has greater permeability for $O_2$ will allow for a correspondingly smaller total area of diffusion cover in a pond cover. For larger ponds, the diffusion cover modules or diffusion cover portions are preferably spaced around the pond, such as by having equal spacing between each diffusion cover module. Distributing the diffusion cover modules or portions around the pond is beneficial for preventing a localized increase in $O_2$ concentration that might inhibit algae growth. The amount of diffusion cover (or diffusion cover modules) can also be expressed relative to the surface area of the pond cover, as opposed to the surface area of the pond. Relative to a surface area of a cover, the portion of the cover corresponding to a diffusion cover portion or module can be about 35% or less of the cover, or about 25% or less, or about 20% or less, or about 15% or less, or about 10% or less.

In another aspect, a non-selective diffusion cover (or alternatively an environmental cover) can be employed that takes advantage of the relative concentration, use, and build-up of $CO_2$ and $O_2$ in the pond. In this case, the cover would be made impermeable to both gasses in an initial section where $CO_2$ is introduced into the pond (typically though some sort of sparger along the bottom and/or within a sump system). As the algae travels along the pond, $CO_2$ is used up and $O_2$ is created. At a downstream location, the oxygen will increase in concentration to the point where it begins to inhibit growth. In advance of this downstream location, $CO_2$ introduction can be ceased, allowing the $CO_2$ concentration to begin to decrease. Alternatively, if $CO_2$ introduction is occurring primarily at one or a few source locations, the concentration of $CO_2$ will decrease as the distance from the $CO_2$ source(s) increases. After allowing the $CO_2$ concentration to decrease, the pond cover may include an open section for free gas exchange to the environment where excess oxygen is purged quickly down to normal atmospheric levels. Since gas exchange in an open section is rapid, "purge" sections that are relatively small compared to the total pond area and/or the total cover area can allow for sufficient removal of oxygen. Subsequently, $CO_2$ is added again, and as flow of both gas and liquid will primarily be in the downstream direction, little back-mixing and loss of $CO_2$ to the free gas exchange section will occur. Since gas-phase concentration equilibration can occur quite rapidly in sections without any gas impermeable cover, the free gas exchange sections can be limited to less than 25%, or less than 20% or less than 15% or less than 10% of the total pond surface area. The resultant cover sections will allow increased use of $CO_2$ over a non-covered pond and higher concentrations averaged over the entire pond area, but minimize inhibition of algae growth by oxygen. The amount of gas interchange vs. gas impermeable area would be managed to match the optimal growth characteristics for a specific species, which can vary among the many species of algae.

Product Recovery Cover

Still another type of cover module (or portion of a cover) is a product recovery cover module or cover portion. A product recovery cover module or cover portion can be used to facilitate separation and recovery of a lipid product from the pond. Lipids tend to be produced in higher amounts during time periods when the algae lacks sufficient quantities of one or more components required for photosynthetic growth, such as during a period of nitrogen or nutrient deprivation or during other times when biochemical triggers are employed to alter the algae growth.

One option for a product recovery module is a module for collecting a product that evaporates and then condenses on the bottom surface of the module (i.e., the surface of the module facing the pond). This would be typical of light products that rapidly evaporate such as small chain oxygenates or hydrocarbons. In this option, it is preferable for the product recovery module not to contact the surface of the pond. Such a product recovery cover module or cover portion typically has a surface facing the pond that is hydrophobic and lipophilic. Such a surface facilitates condensation of hydrocarbons, lipids, and other products on the bottom surface of the product recovery cover. For example, during daylight hours, an increased vapor pressure of hydrocarbons is typically formed in a space between the cover and the pond. A hydrophobic and lipophilic surface encourages condensation of hydrocarbons on the surface in preference to water. In one case, the bottom surface of the product recovery cover portion or cover module has a slight incline moving from an edge of a module to the center or another interior point, or from one edge of the module to the other edge. The incline allows condensed hydrocarbon to flow along the surface of the cover to an edge, such as an edge that includes a product recovery channel. Due to the incline, the edge with the product recovery channel is at a lower height than an interior point on the surface of the module. The product recovery channel accumulates condensed product in a liquid phase either directly or through wicking action of a material in the product collection channel. The hydrocarbon, lipid, or other condensed product entering the product recovery channel then flows into a collection chamber. The flow of condensed product from the recovery channel into the collection chamber can be gravity assisted. Alternatively, a small negative pressure can be used to induce the flow. Some water may also enter the product recovery channel, but the overall concentration of hydrocarbon in the product recovery channel is enhanced relative to the amount of hydrocarbon in the pond. This water will typically also phase separate, allowing for simplified recovery of the desired condensed product. Optionally, an additive can be added to the hydrocarbon after entering the product recovery channel and/or the collection chamber in order to inhibit organisms that might feed on the product.

Another type of product recovery module is designed to contact the pond surface only during recovery of whole algae that have been concentrated on the surface. Here, the product recovery module resides above the surface of the pond during algae growth. The product recovery module is then lowered into contact with the pond when it is desirable to harvest algae from the pond surface. The bottom surface of the product recovery module includes a membrane for capturing algae cells. Typically, the membrane or cover module is designed to have a high binding energy to molecules typical of algae membrane cell walls in comparison with the binding to water. The membrane or cover module may contain or be coated with a material that algae would adhere to through bounding of the cell membranes or by physical absorption. During product recovery, algae that contact the bottom surface of the product recover module are bound to the membrane surface. The membrane surface is then raised out of the water, thus separating the algae from the majority of the water. The algae bound to the membrane can then be further processed in a desired manner, such as by drying the algae or by washing the membrane with an appropriate solvent to remove the algae. The dried and/or washed algae are then ready for subsequent processing to convert the algae biomass into desired products. The recovery module is held not in contact with the surface for most of the algae growth cycle, and is then lowered to touch the surface only when recovery is desired. While it is desirable to remove as much of the algae as possible, it is not required as it may be just as effective to regularly remove a percentage of the total algal culture, reducing the concentration, and thus allowing the remaining cells to further divide, grow, and produce more products. This periodic removal can be done over many cycles spanning many days allowing for semi-continuous production of harvested algae cells.

A product recovery module can also take advantage of capillary action to assist in product removal. In this type of product recovery module, the bottom surface of the module is typically a lipophilic surface that is in contact with the pond surface or in close proximity. The lipophilic surface of the product recovery cover is used to "skim" the surface of the pond for secreted products. The hydrocarbons skimmed from the pond surface attach to the lipophilic surface and are then transported to a product recovery channel as described above. The flow of products to the product recovery channel can be enhanced by raising the product recovery module in a manner so that gravity can assist in transport of the product. An advantage of this type of arrangement is that secreted products are removed quickly, allowing the secreted products to be collected before the products evaporate, degrade, or are consumed by other organisms that are prevalent in the pond environment.

This type of approach for skimming hydrocarbons from the surface of the pond is effective when algae are grown for a majority of the time in order to increase the total number and biomass and then, for a selected smaller amount of time, are induced to produce and secrete products via chemical or biological triggers such as changes in nutrients, salinity, pH, or temperature. This type of product recovery cover can then be employed to rapidly accumulate the product and remove it from the pond after which, potentially, another growth cycle can occur. This operation would be employed where the algae have been engineered to allow for "triggered secretion" of products (which may be oils, fatty acids, triglycerides, or other valuable chemicals). Triggered secretion would allow for safe accumulation of desired products within the safety of the algae cells and then, in response to specific triggers, rapid secretion and collection by the pond cover. Potentially, this type of strategy for triggered secretion and subsequent product recovery allows one to avoid, or minimize, reseeding the algal culture through another cycle of inoculation, growth and accumulation. Instead, this type of triggered secretion and product recovery allows for a "continuous-batch" type process that is enabled by harvesting of the product without destruction of all or most of the algae. Under many types product recovery conditions, a substantial portion of the algae in a pond are removed and/or destroyed by a product recovery process. By contrast, triggering secretion of product followed by product skimming can allow for product recovery while removing or destroying 50% or less of the algae in a pond, or preferably 25% or less of the algae in a pond. This can allow the algae concentration after product recovery to be at least about 50% of the concentration prior to triggering secretion, or at least about 75% of the concentration prior to triggering secretion.

A pond cover could be composed entirely of product recovery modules, but this is typically not preferred. It is noted that the total concentration of algae in a pond is low relative to the volume of the pond. The total concentration of products produced by algae is similarly low relative to the volume of the pond. As a result, collection of algae and/or algae products at one or a few locations in a pond cover is typically sufficient. The surface area of the pond covered by a product recovery module or cover portion can be low relative to the total surface area of the pond, such as about 10% or less of the surface area of the pond, or about 5% or less. The portion of the pond covered by a product recovery module can vary depending on the type of module. For a well-mixed pond with good flow characteristics and a low concern for loss of algae products, a single product recovery module corresponding to less than 5% of the pond surface area may be sufficient. Alternatively, if faster product recovery is desired, a greater percentage of the pond can be covered by product recovery modules, such as by evenly spacing a plurality of modules at various locations above or on the surface of the pond. Of course, additional portions of the pond may be covered by other types of cover modules or cover portions, so that the total amount of the pond that is covered by the cover system as a whole corresponds to a desired amount, such as at least about 75% or at least about 90%. With respect to the total area of a pond cover system, the product recovery cover portion can correspond to about 15% or less of the area of the cover, or about 10% or less, or about 5% or less.

Thermal Management

A variant of the environmental module or cover portion is a thermal management cover module or portion. During daylight hours, one of the typical environmental impacts on a pond is the temperature impact from exposure to radiant energy. Another typical impact is the loss of energy back to the environment due to radiative or convective cooling of the pond. Thermal management cover portions or cover modules can be used to mitigate the effects of these processes, thus allowing for improved control over the temperature of the pond. The thermal management cover modules can be distinct from the environmental cover modules, or the same module type can serve as both a thermal management module and an environmental cover module.

One thermal management technique is to limit the amount of radiation that reaches the pond surface that is not useful for algae growth, such as ultraviolet radiation. These non-useful types of radiation can be reflected by the outer surface of the pond cover, which reduces the amount of energy absorbed by the pond. This can be accomplished by providing a UV and IR reflective layer as part of the cover. The UV reflective layer should have little or no impact on other types of light transmitted by the cover. The ability to reflect UV and IR radiation is known in the art and employed in industrial applications such as manufacture of automobile windows.

Another thermal management technique is to have a thermal reflective coating on the inner surface of the cover. A thermal reflective coating on the inner or bottom surface of the cover will inhibit infrared radiation losses by the pond to the environment. A pond typically exchanges heat with the surroundings in a continuous manner. The presence of the cover as a barrier reduces or minimizes the amount of convective cooling and/or cooling due to evaporation. The use of a thermal reflective coating complements the reduction in cooling by reflecting radiative energy emitted by the pond back into the pond surface. Various types of thermal reflective coatings are known and can be sprayed on a surface. Potentially suitable coatings are made, for example, by 3M of St. Paul, Minn.

Another form of thermal management employs materials, like specific phosphorescent compounds, that absorb light that is outside of the visible range and then re-emits that radiation in the form of visible light. Such materials can be employed in a layered structure designed to produce additional useful photons aimed at the algae while minimizing incoming heat radiation.

Still another form of thermal management is to capture additional sunlight for conversion into electricity. One option is to integrate solar collectors into one or more side walls of the pond. One of the pond sidewalls can extend above the overall level of the liquid plus the cover or cover modules, such as by having a pond sidewall that extends an additional foot of height above the level of the pond surface and/or cover. Optionally, for a pond in the northern hemisphere, this wall is oriented to face south in order to increase sun exposure, such as by having the long axis of the pond oriented in a substantially east-west direction. Optionally, at least the portion of this wall extending above the height of the pond and/or cover is inclined at an angle of about 10 to about 45 degrees, as opposed to being vertical. The portion of the wall extending above the pond and cover provides surface area for deploying conventional photovoltaic cells, such as a thin strip of photovoltaic cells a few inches high and 10s to 100s of feet long, while consuming little or no more land than was already required for the pond.

Other types of devices for converting solar radiation into electricity can also be incorporated into the cover or cover modules. For example, thin film solar cells (such as organic photovoltaics) could be applied to the outer surface of the cover in locations where the cover does not transmit radiation through to the pond. Organic photovoltaics have been known for some time. Organic photovoltaics are typically not as efficient as the most efficient semiconductor based photovoltaic cells, but organic photovoltaics are still effective for converting solar energy into electricity. An advantage to such polymeric materials is that they can be "printed" or deployed at a variety of scales from meters in size, to centimeters or even printed in widths approaching micron-sized stripes. The effect of reducing the width of these structures is that they can, when sufficiently small, appear largely transparent. For example, windows coated with such thin width structures are capable of collecting and converting solar energy while still allowing some illumination to pass through. Suitable materials for this purpose are organic photovoltaics supported in plastic—such as those available from Konarka Technologies of Lowell, Mass.

If organic photovoltaic type structures are coated onto the cover, such as on an environmental cover portion or cover module, the resulting cover portion or module can both collect solar energy and enhance algae growth by reducing the overall intensity of light. Additionally, use of organic photovoltaics on a portion of a module may assist in producing the intermittent light and "flashing light" effect. As noted above, algae typically do not grow optimally in continuous high-intensity sunlight. Mixing algae in ponds under turbulent conditions mitigates this, as does turning a light on and off rapidly. However, it is difficult to guarantee that uniform mixing will occur over massive multi-acre pond structures. Similarly, "turning off" sunlight is not practical for obvious reasons. Instead, a large pond's natural dynamics can be meshed with solar collection. In one aspect, more quiescent areas of the pond are covered by organic solar collection modules such that the module has some sections that substantially block sunlight while other sections are largely transparent to light. In such case, the width of the organic photovoltaic material is selected so that the average rate of algae mixing is matched to the on-off timing induced by flowing underneath the stripes of photovoltaic collector. In other words, the width of the organic photovoltaic material is selected based on the expected distance required for algae in the pond to change height from near the surface of the pond to a lower portion of the pond. It is not necessary to cover the entire, or even a large percentage of the total pond with such photovoltaic materials. The photovoltaic material can be deployed in an amount sufficient to generate electricity used for operation of the pond system. Optionally, the photovoltaic material is deployed in areas of the pond where it is expected that mixing may be less efficient than desired.

Still another option is to use passive heating and cooling to assist with temperature management. Where a portion of the incident sunlight reaches the walls and/or floor of the pond, the wall and floor surfaces can be used to capture energy. The wall and floor surfaces can be made from a high heat capacity material that is colored to enhance absorption of incident radiation. During daylight hours the walls and/or floor can absorb radiant energy. This energy can be emitted back into the pond at night.

Yet another type of thermal management is to use heat exchange to moderate the temperature of the pond. In this type of thermal management, a typical heat transfer fluid is pumped through pipes embedded in the walls and/or floor of the pond. During the hottest hours of the day, the heat transfer fluid absorbs heat from the pond, reducing the amount of temperature rise. The fluid is then pumped back through the pipes in cooler conditions. This type of thermal management may be especially useful in climates with large day/night variations in temperature and strong evaporative cooling such as arid and desert environments. The power for this active type of thermal management can be provided, for example, by solar modules as described above. This allows the active thermal management to be used without requiring addition utilities or other energy inputs.

The present invention contemplates cover systems and methods employing the same which comprise combinations of the various cover portions or modules described above. For example, the invention encompasses cover systems and methods comprising the following combinations of the cover portion or modules described above:
1, "environmental" and "diffusion"
2, "environmental" and "thermal management"
3, "environmental" and "product recovery"
4, "diffusion" and "thermal management"
5, "diffusion" and "product recovery"
6, "thermal management" and "product recovery"
7, "environmental", "diffusion" and "thermal management"
8, "environmental", "product recovery" and "thermal management"
9, "diffusion", "thermal management", and "product recovery"
10, "environmental", "diffusion", "thermal management" and "product recovery"

Passive and Active Mixing

Algae typically use only a percentage of the solar radiation incident on a pond surface, and can in fact be inhibited by excess solar radiation. For algae in a pond, it is often beneficial to allow the algae to spend a percentage of time during daylight hours away from exposure to sunlight. In general, algae should experience a continuous cycle of intermittent light exposure where the algae spend more time in the dark than in the light and—depending on the identity of the algae and whether the goal is to maximize growth or lipid production—as much as ninety percent of the time in the dark and 10 percent of the time in the light. This can be achieved by introducing turbulence into the pond so that the algae continuously rise and fall relative to the surface of the pond.

Closed photobioreactors typically use combinations of pumps and tubes to induce high Reynolds numbers (a measure of turbulence) within the photobioreactor. This results in good mixing so that the exposure of algae to incident light is controlled. By contrast, a conventional open pond typically generates turbulence and potential energy through the lifting action of a paddle wheel (or similar device), but typically does not maintain uniform, optimized turbulence. As the water flows around a large pond, frictional losses result in slow dissipation of the turbulent eddies and circulation currents within the pond. As a result, algae far from the paddle wheel may not be well-mixed, and therefore the algae in the pond may experience large variances in the amount of light exposure.

The above problems are mitigated by adding mixing devices to a pond. The mixing devices enhance the turbulence within the pond and facilitate maintaining favorable conditions for capture of incident solar radiation by the algae. Static or passive devices can be used such as static mixers, cavitation devices, baffles or the like. The passive devices are designed to maintain flow in the pond in the turbulent region over a portion of the pond volume by introducing eddies into the flow. Preferably, the passive devices allow a turbulent flow to be maintained within the pond for as large a pond volume as possible. The passive devices may be incorporated into the floor and/or the walls of the pond structure. Preferably, the passive structures are located underneath the surface of the pond. This reduces or prevents turbulence at the surface where oil may be separating from water, or where a specific differential is desired between the height of the water level and the height of the bottom of the cover.

Another option is to use active mixing devices in one or more locations in the pond. For example, high efficiency, slow turning in-water propellers could be added to aid mixing. A slow turning propeller refers here to propellers that turn slowly enough to mitigate or avoid damage to the algae within the pond. The speed of such device will be dependent on the species of algae and it's resistance to lysing by shear forces. These active mixing devices are added to the extent needed to generate a desired amount of turbulence throughout the pond. Such mixing devices may be relatively more efficient in a pond as compared to a photobioreactor. In a photobioreactor, due to the relatively small volume as compared to the surface area of the enclosing walls, drag from wall effects and overall pressure drop are typically far higher per distance traveled as compared to a pond.

The operation of active mixing devices is optimized in relation to growth and harvesting cycles that occur over a course of a day, or over the algae life cycle. For example, in night time conditions, the mixing devices can be shut off. Since there is no incident sunlight, the light intensity experienced by the algae is not impacted by the presence or absence of sufficient turbulence. In this situation, the paddle wheel for a pond may provide sufficient turbulence to promote growth in a non-photosynthetic environment. In another example, algae in a pond may go first through a cell division/cell growth stage. A change in nutrients, pH, or another trigger is then be used to cause the algae to enter an oil production/secretion phase. During the first phase, additional in-water propellers are activated to improve the growth rate of the algae. In the second phase for oil production, the water propellers are stopped, resulting in reduced mixing so that oil can float to the surface and separate more easily. A combination of active and passive mixing devices may be also be used.

The depth of a pond also plays a factor in the amount of mixing that is needed to achieve a desired level of turbulence. In the shallow type ponds that are often used for algae growth, the depth of the growth pond can have a substantial impact on the Reynolds number for the pond. For example, consider a pond that has a depth of 30 cm and a Reynolds number of about 1000. If the depth of the pond is reduced to 10 cm, the Reynolds number of such a pond can increase to about 3000. For a conventional pond without a cover, obtaining increased turbulence by reducing the pond depth would also lead to increased evaporation relative to the volume of the pond. For a given volume of water, decreasing the depth of the pond requires a corresponding increase in surface area. Since evaporation is proportional to exposed surface area, decreasing the depth of a pond leads to a corresponding increase in evaporation at constant pond volume. By using a cover as a barrier to reduce evaporation, the benefits of a reduced pond depth can be achieved while mitigating the negative side effects related to evaporation.

The invention encompasses cover systems and methods employing the same as described in paragraph [00069] above in combination with any of the passive or active mixing devices and methods described above.

Types of Algae

Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. For example, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

Algae oils, primarily lipids, are typically contained in algae in the form of membrane components, storage products, and metabolites. Certain algal strains, particularly microalgae such as diatoms and cyanobacteria, contain proportionally high levels of lipids. Algal sources for the algae oils can contain varying amounts, e.g., from 2 wt % to 60 wt % of lipids, based on total weight of the biomass itself.

EMBODIMENTS

Accordingly, the present invention at least includes one or more of the following embodiments.

Embodiment 1

A system for growing algae, comprising: a pond for growing algae in communication with an ambient environment; and a cover system covering at least 10% of a surface of the pond.

Embodiment 2

A system according to embodiment 1, wherein the cover system comprises a plurality of cover modules.

Embodiment 3

A system according to embodiments 1 or 2, wherein the cover system comprises a first cover portion that selectively allows diffusion of $O_2$ relative to $CO_2$.

Embodiment 4

A system according to embodiment 3, wherein the area of the first cover portion is selected based on the formula:

Diffusion Cover Area=(Pond Volume)×(Algae Concentration)×($O_2$ Generation Rate Per gram of Algae)/($\Delta O_2$ Concentration)×($O_2$ Diffusion Rate).

Embodiment 5

A system according to embodiment 3 or 4, wherein the first cover portion comprises a frame material providing structural support for a material that facilitates selective diffusion of $O_2$ relative to diffusion of $CO_2$.

Embodiment 6

A system according to any of the above embodiments, wherein the cover system is configured to support an $O_2$ concentration in a gas phase volume between the cover system and a surface of the pond that is greater than an $O_2$ concentration of the ambient environment by about 10% or less, and the cover system is configured to support a $CO_2$ concentration in the gas phase volume that is greater than a $CO_2$ concentration in the ambient environment by at least about 10%.

Embodiment 7

A system according to any of the above embodiments, wherein the cover system comprises a second cover portion that includes a thermal management coating on a surface of the second cover portion, the thermal management coating comprising a coating that absorbs or reflects at least one of ultraviolet light, actinic light, or infrared light.

Embodiment 8

A system according to embodiment 7, wherein the thermal management coating comprises a coating that absorbs at least one of ultraviolet light or actinic light and emits actinic light of a wavelength different from the absorbed light.

Embodiment 9

A system according to embodiment 7 or 8, wherein the thermal management coating comprises photovoltaic cells.

Embodiment 10

A system according to any of embodiments 7 to 9, wherein the thermal management coating comprises a coating that reflects infrared light, the coating being located on a surface of the second cover portion that faces the surface of the pond.

Embodiment 11

A system according to any of the above embodiments, wherein the cover system comprises a third cover portion that facilitates capture of hydrocarbons generated by the algae in the pond.

Embodiment 12

A system according to embodiment 11, wherein a surface of the third cover portion is in contact with a surface of the pond during capture of hydrocarbons.

Embodiment 13

A system according to embodiment 11 or 12, wherein a surface of the third cover portion that faces a surface of the pond is a hydrophobic and lipophilic surface.

Embodiment 14

A system according to any of embodiments 12 to 14, further comprising a product recovery channel at an edge of the third cover portion, the third cover portion being inclined so that the product recovery channel is at a lower height than an interior point of the third cover portion, the product recovery channel including an opening to allow fluid communication between the product recovery channel and a surface of the third cover portion that faces a surface of the pond.

Embodiment 15

A system according to any of the above embodiments, wherein the cover system comprises a fourth cover portion that allows at least about 50% of incident actinic light intensity to pass through to a pond surface.

Embodiment 16

A system according to any of the above embodiments, further comprising: at least one cover support structure that at least partially supports the cover system; a primary mixing device configured to generate a flow within the pond; and at least one secondary mixing device attached to a floor of the pond or a wall of the pond.

Embodiment 17

A system according to embodiment 16, wherein the at least one secondary mixing device comprises a passive mixing device.

Embodiment 18

A system according to embodiment 16 or 17, wherein the at least one cover support structure comprises a divider separating the flow within the pond, the divider including a support lip for supporting the cover system.

Embodiment 19

A system according to any of embodiments 16 to 18, further comprising a plurality of solar collectors mounted on a wall of the pond, the solar collectors being mounted on a wall portion extending above the surface of the cover system.

Embodiment 20

A system according to any of the above embodiments, further comprising a photovoltaic film deposited on at least a portion of the cover system.

Embodiment 21

A method for managing a pond, comprising the following steps: covering a first portion of a pond with a first cover portion that allows at least 50% of actinic light to pass through the first cover portion; and covering a second portion of the pond with a second cover portion that selectively allows diffusion of $O_2$ relative to $CO_2$.

Embodiment 22

A method according to embodiment 21, further comprising mixing the pond with a mixing device located under the first cover portion or the second cover portion.

Embodiment 23

A method according to embodiment 22, further comprising: generating electricity by converting solar energy using a photovoltaic device; and powering the mixing device using the generated electricity.

Embodiment 24

A method according to any of embodiments 21 to 23, further comprising: covering a third portion of the pond with a cover portion that facilitates product recovery; and collecting a hydrocarbon product.

Embodiment 25

A method for managing a pond, comprising the following steps: covering a first portion of a pond with a first cover portion that allows at least 50% of actinic light to pass through the first cover portion; covering a second portion of the pond with a second cover portion, the second cover portion having a lipophilic surface that facilitates capture of hydrocarbons generated by the algae in the pond; exposing algae within the pond to conditions effective for accumulation of a product, the algae having a first algae concentration within the pond; triggering secretion of the accumulated product; and collecting the secreted product using the second cover portion, wherein the algae within the pond have a second algae concentration after triggering secretion of the accumulated product and collection of the secreted product, the second algae concentration being at least about 50% of the first algae concentration, preferably at least about 75% of the first algae concentration.

Embodiment 26

A method according to embodiment 25, wherein collecting the secreted product using the second cover portion comprises: lowering the second cover portion so that at least a portion of the lipophilic surface is in contact with a surface of the pond; collecting the secreted product using the second cover portion; and raising the second cover portion.

Embodiment 27

A system according to any of embodiments 1 to 20, wherein the system increases $CO_2$ utilization in the pond by at least about 5% relative to the pond in an uncovered state, preferably by at least about 10%, and more preferably by at least about 20%.

Embodiment 28

A system according to any of embodiments 1 to 20 or embodiment 27, further comprising at least one $CO_2$ source within the pond.

Embodiment 29

A system according to Embodiment 28, wherein the cover system further comprises at least one gas exchange opening, the at least one gas exchange opening being closer to a nearest $CO_2$ source in a downstream flow direction than to a nearest $CO_2$ source in an upstream flow direction.

Embodiment 30

A system according to any of embodiments 1 to 20, wherein the system reduces at least one of water lost due to evaporation from the pond or water gained due to absorption of rainwater by the pond by at least about 5% relative to the pond in an uncovered state, preferably by at least about 10%, and more preferably by at least about 20%.

Prophetic Example

In this prophetic example, a raceway pond is used with a length to width ratio of 15. The pond has a width of 20 meters, and therefore a corresponding length of 300 meters. The depth of the pond is 20 cm. A central divider in the pond establishes raceways having an equal width of about 10 m in the pond.

The long axis of the pond is oriented roughly along an east-west axis. The south facing wall of the pond includes an extension above the surface of the pond. Photovoltaic cells are mounted on the wall to provide energy for mixing devices in the pond. One of the mixing devices is a paddle wheel that establishes a turbulent flow within the pond. Additionally, several active mixing devices are distributed throughout the pond to further assist in generating turbulence. A plurality of $CO_2$ injection sources provide $CO_2$ for algae growing within the pond.

Initially, the pond is used for algae growth without a cover. Starting from an initial algae concentration of 100 ppm, algae is grown for 24 hours. The utilization for the $CO_2$ injected into the pond is 80%. Based on the algae growth, the algae concentration increases to a value larger than 100 ppm.

The algae concentration of the pond is then reduced back to 100 ppm, such as by diluting the pond or removing algae from the pond. A cover system is then placed over the pond. The cover system is in the form of a group of cover modules. The bottom of the cover system has an average height above the surface of the pond of about 2 cm. Based on the pond depth of 20 cm, the gas volume between the bottom of the cover and the pond surface represents a little less than 10% of the total volume below the cover. Most of the cover modules have a rectangular shape and bridge the full width of the pond. For the rectangular modules, the central divider provides additional support in the center of the module. In addition to the modules bridging the full width of the pond, a few rectangular modules only bridge the distance from an edge of the pond to the central divider. These modules are used opposite the paddle wheel. The paddle wheel area of the pond is not covered. For the ends of the pond, additional rectangular covers can be used, but this example uses the preferred option of having a series of triangular, trapezoidal, or other shaped sections that approximate the curvature of the end of the pond. By leaving the paddle wheel area uncovered, approximately 95% of the pond surface area is under a cover module and/or the cover system. Thus, less than 100% of the pond surface area is under the cover system, or less than 99% of the pond surface area is under the cover system.

With respect to the types of cover modules, about 70% of the cover module area corresponds to environmental cover modules. Another about 20% of the cover module area corresponds to diffusion cover modules that selectively permit diffusion of $O_2$ relative to diffusion of $CO_2$. The remaining about 10% of the cover module area corresponds to product collection modules.

After installing the cover system, the algae are grown for another 24 hour period under conditions similar to the growth period without the cover. Due to the cover, the $CO_2$ utilization increases to 90%. The concentration of $CO_2$ in the gas phase below the cover is 430 ppm. Relative to the atmospheric concentration of 390 ppm, this represents at least a 10% increase in the $CO_2$ concentration below the cover. The $O_2$ concentration below the cover is about 21.5%. Relative to the atmospheric concentration of 20.9%, this represents a less than 5% increase in the $O_2$ concentration below the cover.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

What is claimed is:
1. A method for managing a pond, comprising the following steps:
   (i) covering a first portion of a pond with a first cover portion that allows at least 50% of actinic light to pass through the first cover portion;

(ii) covering a second portion of the pond with a second cover portion that selectively allows diffusion of $O_2$ relative to $CO_2$, wherein the area of the second cover portion is selected based on the formula:

Diffusion Cover Area(Pond Volume)×(Algae Concentration)×($O_2$ Generation Rate Per gram of Algae)/($O_2$ Concentration)×($O_2$ Diffusion Rate); and (iii) covering a third portion of the pond with a third cover portion having a lipophilic surface that facilitates product recovery and collecting a hydrocarbon product.

2. The method of claim 1, further comprising mixing the pond with a mixing device located under the first cover portion or the second cover portion.

3. The method of claim 2, further comprising generating electricity by converting solar energy using a photovoltaic device and powering the mixing device using the generated electricity.

4. A method for managing a pond, comprising the following steps:
(i) covering a first portion of a pond with a first cover portion that allows at least 50% of actinic light to pass through the first cover portion;
(ii) covering a second portion of the pond with a second cover portion, the second cover portion having a lipophilic surface that facilitates capture of hydrocarbons generated by the algae in the pond;
(iii) exposing algae within the pond to conditions effective for accumulation of a product, the algae having a first algae concentration within the pond;
(iv) triggering secretion of the accumulated product; and
(v) collecting the secreted product using the second cover portion,
wherein the algae within the pond have a second algae concentration after triggering secretion of the accumulated product and collection of the secreted product, the second algae concentration being at least about 50% of the first algae concentration, and
wherein the area of the second cover portion is selected based on the formula:

Diffusion Cover Area(Pond Volume)×(Algae Concentration)×($O_2$ Generation Rate Per gram of Algae)/($O_2$ Concentration)×($O_2$ Diffusion Rate).

5. The method of claim 4, wherein the step of collecting the secreted product using the second cover portion comprises substeps of (a) lowering the second cover portion so that at least a portion of the lipophilic surface is in contact with a surface of the pond; (b) collecting the secreted product using the second cover portion; and (c) raising the second cover portion.

6. The method of claim 4, wherein the second algae concentration is at least about 75% of the first algae concentration.

* * * * *